United States Patent [19]

Alliger et al.

[11] Patent Number: 4,920,954
[45] Date of Patent: May 1, 1990

[54] ULTRASONIC DEVICE FOR APPLYING CAVITATION FORCES

[75] Inventors: Howard M. Alliger, Melville; Donald J. Ciervo, Levittown, both of N.Y.

[73] Assignee: Sonic Needle Corporation, Farmingdale, N.Y.

[21] Appl. No.: 228,475

[22] Filed: Aug. 5, 1988

[51] Int. Cl.$^5$ ............................................. A61B 17/32
[52] U.S. Cl. .................... 128/24 A; 606/128
[58] Field of Search ............. 128/24 R, 24 A, 303 R, 128/305, 328, 660.03; 604/22

[56] References Cited

U.S. PATENT DOCUMENTS

| | | | |
|---|---|---|---|
| 3,618,594 | 4/1970 | Banko | 128/24 A |
| 3,861,391 | 1/1975 | Antonevich et al. | 128/24 A X |
| 4,223,676 | 9/1980 | Wuchinich et al. | 128/24 A X |
| 4,431,006 | 2/1984 | Trimmer et al. | 128/24 A X |
| 4,750,902 | 6/1988 | Wuchinich et al. | 128/24 A X |

Primary Examiner—Francis Jaworski
Attorney, Agent, or Firm—Howard Paul Terry

[57] ABSTRACT

An ultrasonic device for applying cavitation force to an unwanted material is provided. The device is particularly useful for removing plaque from a human artery wherein a portion of the device can enter an artery and pass through the artery to the vicinity of the plaque. The device includes a solid wire of titanium material, a transducer, a generator for providing vibration energy via the transducer, and a handpiece enclosing the transducer and having a tapered end portion with an exponential surface of slightly concave profile. The tapered end portion is fixedly connected to an inner end of the wire. For human applications, the wire has an overall length in the range of about 5 inches to 40 inches and has a uniform outer diameter in the range of about from 0.015 inches to 0.040 inches. The device includes a catheter assembly having a catheter tube enclosing the wire and includes a container unit mounted on the tapered end portion of the handpiece. The container unit has a fluid chamber for receiving a contrast material which passes through the chamber, through the catheter tube, to the outer end tip portions of the wire and tube in the area of the plaque to be removed. The container unit also has a coupling unit forming an outer end wall thereof having a fixed portion and a rotatable knob portion for moving the catheter tube axially relative to the wire for adjusting the extension of the outer end tip portion of the wire beyond the outer end tip portion of the catheter tube.

14 Claims, 3 Drawing Sheets

STEPPED

FIG. 7a

CONICAL

FIG. 7b

2X TAPER

FIG. 7c

ULTRASONIC DEVICE FOR APPLYING CAVITATION FORCES

BACKGROUND OF THE INVENTION

The invention generally relates to an ultrasonic device, and in particular the invention relates to an ultrasonic cavition device having a wire which is composed of a metal having a relatively low modulus of elasticity such as titanium. The wire has a length and a diameter dimensioned for specific applications of removal of unwanted material. One application, for example, is the removal of plaque from a human artery by the action of fluid cavitation. Another application, for example, is the removal of contaminants from otherwise inaccessible areas of industrial parts, such as aerospace parts.

Related U.S. Pat. Nos. include:
3,352,303, issued Nov. 14, 1967,
3,565,062, issued Feb. 23, 1971,
3,589,363, issued Jun. 29, 1971
3,618,594, issued Nov. 9, 1971,
3,861,391, issued Jan. 21, 1975,
4,474,180, issued Oct. 2, 1984, and
4,660,573, issued Apr. 28, 1987.

Related publications include:
(1) "A Critical Appraisal of Methods for Disruption and Extraction of Urinary Calculi Especially with Ultrasound", by Harold Lamport and Herbert F. Newman, The Yale Journal of Biology and Medicine, Volume 27, Number 5, Jun., 1955.
"A New Method to Cure Thrombi by Ultrasonic Cavitation ", by U. Stumpff, R. Pohlman and G. Trubestein, Ultrasonics International 1975 Conference Proceedings.
(3) "Preliminary Feasibility Studies Using an Ultrasonic Device for Endarterectomy", by Harry L. Finkelstein, M.D., et al, The Mount Sinai Journal of Medicine, Volume 46, Number 2, Mar. -Apr., 1979.
(4) Technical Support Package Entitled "Speculation on Ultrasonic Disintegration of Arterial Deposits", George C. Marshall Space Flight Center, Marshall Space Flight Center, Ala. 35812, Winter 1983, Volume 8, Number 2, MFS-25161.

The prior art devices which have endeavored to remove unwanted material from the human body or other inaccessible areas have severe limitations. In most of these devices the sonic wave guide or active probe is short and rigid. In the case of ureter stones, the active tube or wire is about 45 cm long (18"), but is still fairly rigid. The urinary duct is straightened by the metal wire insertion. This cannot be the case, however, if one is to reach the coronary arteries percutaneously by entering a blood vessel at the neck or armpit. Similarly, it is not possible to thread rigid wire down the leg when the artery or vein to be cleaned is sinuous. In these instances, the ultrasonic waveguide or wire must be long, narrow and highly flexible in order to pass through the vessel without causing damage. Further, because there is a standing soundwave in the wire, the metal composition must provide minimum attenuation of the sonic energy. In layman's terms, the metal must be capable of ringing like a bell. Experiments have shown that this property is especially important when the wire is bent, since bending greatly increases the tendency for energy in the sound wave to be dissipated as heat and a significant temperature rise would not be tolerable.

The process of transmitting sound waves into arteries of the heart or leg by inserting a wire through the blood vessels was first tried in the early 1960's. At that time standard ultrasonic instruments became available for laboratory homogenizing and emulsifying. These devices were portable ultrasonic probes, about ½" diameter, and had about 200 times the intensity or vibration amplitude of the more common ultrasonic tank cleaners. A long wire could be attached to the vibrating end of these probes, and the wire then maneuvered through the blood vessels. Energizing the probe would in turn activate the wire. Although reaching occlusions in the leg by wire was sometimes successful, the process of plaque removal was not. Energy transmitted to the vibrating tip was insufficient to produce the necessary cavitation (bubble collapse) for disrupting or liquefying plaque. Removal of simple blood clots or thrombi in the leg, a far less demanding application, was also unsuccessful. For this and other reasons, the device disclosed in U.S. Pat. No. 3,352,303, 1967, "Method For Blood Clot Lysis" had significant limitations. Arterial plaque could be removed by ultrasound as discussed in publication number 3 cited above, but the procedure was performed with a relatively short rigid probe and it was necessary to completely open the artery and expose the occlusive plaque.

The idea of threading an ultrasonic wire into blood vessels has been tried many times in the last 25 years, and with good reason. Arteriosclerosis is the number one killer in the western world. Unfortunately, a vibrating percutaneous wire system never showed promise in treatment of this disease, nor did it provide data suitable for reporting in the scientific literature. When power was increased to the wire, it overheated, and moreover, tended to vibrate itself apart. Well before reasonable displacement was achieved at the tip, the wire broke, usually at the attachment point to the horn.

In publication 4 cited above, the authors suggest that removing arterial deposits by ultrasonic disintegration would be an excellent idea. After a number of investigations, they concluded that this area of ultrasound was apparently virtually unexplored.

U.S. Pat. No. 4,474,180, 1984, *Apparatus for Disintegrating Kidney Stones*, attempts to increase the useful life of wire in kidney stone breaking by utilizing a long damper tube. This tube closely fits around the wire near its attachment to the horn, and reduces undesirable transverse vibration. However, a close fitting tube placed anywhere along the wire would limit both longitudinal as well as lateral motion, and therefore the tip displacement would be much reduced. A separate catheter referred to in the same patent, is specifically made loose to avoid such a difficulty. In U.S. Pat. No. 3,861,391, 1975, *Apparatus for Disintegration of Urinary Calculi*, no mention is made, or suggestions offered, as to the type of metal to be used in this patent or the previously cited patent. It was not important to the inventor. The same is the case for U.S. Pat. No. 4,660,573, 1987, *Ultrasonic Lithotriptor Probe*.

Because of its great strength and high proportional limit, stainless steel and other high strength steels were used as wire or waveguides in past blood clot disruption experiments. These metals are now in standard use as kidney stone breakers. In U.S. Pat. No. 3,565,062, 1971, *Ultrasonic Method and Apparatus for Removing Cholesterol and Other Deposits from Blood Vessels and the like*, the inventor goes into detail as to how and why his device works. He suggests the use of Monel and stainless steel as waveguides. Similarly in U.S. Pat. No.

3,618,594, 1971, *Ultrasonic Apparatus for Retinal Reattachment* the inventor suggests the use of Monel for the active probe. Similarly in U.S. Pat. No. 3,352,303, cited above, the inventor suggests stainless steel or Monel. Also in U.S. Pat. No. 3,589,363, the vibration transmitting material is suggested to be Monel metal with only the operative tip comprising "an extremely hard, sterilizable material, such as titanium".

One problem with certain prior art ultrasonic device is that the wire, which is relatively short and relatively rigid, is not suitable for entering into an artery in the armpit or neck area of the human body, and for passing through the artery to the vicinity of the heart.

In one ultrasonic kidney stone device, U.S. Pat. No. 3,861,391, cited above, the wire is specifically designed to increase whipping motion at the tip so as to break the stones faster. Kidney stones however, for the most part are not broken by cavitation, or the making and breaking of bubbles, but by pounding or a jackhammer effect.

In U.S. Pat. No. 3,565,062, cited above, the inventor recognizes that heat generation is a problem during blood clot removal and indicates that discrete points on the wire waveguide will glow red hot. The inventor "solves" the problem by constantly changing the frequency so that nodes and anti-nodes on the wire physically shift, as well. But unfortunately, the wire, for the most part, will only resonate at the fundamental frequency for which it was designed, and changing frequencies is tantamount to turning the apparatus on and off.

In publication 2 cited above, the authors discuss dissolving thrombi utilizing an ultrasonic waveguide but apparently if no liquid is supplied via the waveguide, the temperature becomes so high that the wall of the vessel can be burned.

Another problem encountered in the perecutaneous removal of plaque, or other applications of this kind, is the attachment of the wire to the horn. Since the horn and wire cannot be fabricated as one continuous piece, energy losses will occur at this junction. A similar problem arises with devices for kidney stone breaking. Harmonic generation and reflections occur at the attachment site, and these attenuate the fundamental wave and cause power loss. When the necessary amount of power is finally delivered to the wire tip, the attachment point will usually heat up and break in a few seconds unless cooling water is applied. This is the case with both kidney stone breaking and cataract removal, but would be even more noticeable in the plaque removal process where a small diameter and longer wire is necessary and the amplitudes required are higher.

Methods of attaching ultrasonic wire and tubes in the past include: brazing, welding, threading, epoxying, and clamping. These were found inadequate in present plaque and blood clot application because, except for threading, each causes too much power loss or heating. Perhaps 90% of the applied energy is wasted in kidney stone breaking, although the high strength metal used as transmitting wire or tubes can withstand the extra stress and heat. Furthermore, it is not difficult to cool the vibrating wire with running water, or saline, as a kidney stone is being sonicated.

Brazing or soldering makes a poor bond with titanium. Brazing, too, tends to anneal stainless steel so that some of the sound wave is damped or reflected. Welding temperatures required for titanium, change the grain structure at the heated junction, producing non-linearity as well as weakening the metal. Both epoxy bonding, and attachment by clamping or thumb screw, result in too much loss and heat. Producing a screw thread on titanium wire 1 mm in diameter is not possible at present.

In U.S. Pat. No. 4,474,180, cited above, an improved method of attaching wire to a vibrating ultrasonic horn is described. The wire "life" is prolonged to a little over a minute, rather than the previous time to breakage of 20 seconds. This performance is clearly not acceptable in our projected blood vessel applications where much longer times will likely be needed to destroy arterial plaque. Moreover, just the threat of wire breaking during insertion into the heart arteries is unacceptable.

SUMMARY OF THE INVENTION

We have developed an ultrasonic system which will remove arterial plaque and blood clots and be useful in treating other diseases as well. It was found that although a long wire seemed to break easily when sonic power was applied, wire strength, per se, was not the necessary or overriding factor. As it turned out, the modulus of elasticity and the actual wire diameter are the key elements. Other findings and improvements also aided in this difficult ultrasonic application.

Collagenous tissues such as bone, cartilage, and, in this case blood vessels, are not easily affected by ultrasonic action or cavitation. Therefore ultrasound transmitted through a wire, if sufficient, can selectively disrupt embedded plaque and blood clots while leaving the blood vessels intact. During lysis, the space between wire and its catheter sleeve can be used to evacuate debris, if necessary.

According to the present invention, an ultrasonic cavitation device is provided, which uses cavitation or microscopic bubble action to remove plaque from an artery, and which can enter an artery in the armpit or neck area and pass through the artery to the vicinity of the heart. The present invention is suitable for elimination of plaque or any other form of occlusion in blood vessels or bodily organs as well as unwanted material in inaccessible areas of other items such as industrial parts. Such ultrasonic cavitation device includes a solid wire, which is composed of a metallic material having the characteristics of titanium metal and which has a wire overall length and has a wire outer diameter suitable for the particular application. Such device also has a handpiece which has a tapered end portion that is fixedly connected to the wire for supporting the wire, a transducer disposed within the handpiece for vibrating the wire, and a generator for energizing the transducer.

By using the solid wire as described immediately above, the ultrasonic device according to the invention overcomes the problem of providing a wire suitable for entering into, for example, an artery leading to the occlusion and for passing through the artery to the immediate vicinity of the occlusion.

The results of our recent experiments, revealed that the stress/strain characteristics of titanium alloys were far better for this application than those of high strength stainless steel or other metal alloys like Monel, Inconel, or piano wire (350,000 psi). Titanium is sometimes used as horn or tip material on ultrasonic devices because it is chemically inert, and its hardness resists cavitation erosion. Titanium is also relatively non lossy to sound waves. These are not the particular physical properties, however, that make titanium indispensible as the wire metal in plaque removal or even difficult kidney stone applications, and until now titanium has not been used as a waveguide in these fields.

Titanium has a moderately high proportional limit but combines this characteristic with a low modulus of elasticity. We found that titanium alloys with the lowest modulus of elasticity and not the highest strength, worked best. This finding is rather surprising considering the emphasis in publication 1, cited above, that a metal with a high Young's modulus would be better suited to this application.

At high stress, the stress/strain characteristics of titanium metal remain linear, but more importantly, provide relatively great movement (strain) or displacement. Aluminum has an even lower modulus than titanium, which would appear to make it more useful in this application. But this metal also has a very low proportional limit and, therefore, will break at relatively low stress before it can attain a reasonable tip vibration or displacement. If one is to achieve a particular strain, or tip movement, a lower modulus (indicated by a more horizontal slope in FIG. 3) would permit a lower proportional limit. The reverse is not so simple in practice, however. A higher proportional limit would allow a higher modulus, in theory. But the applied stress or energy in this case is increased to a point which causes unwanted harmonics to appear. As a result, the wire begins to shake and vibrate laterally since it does not transform all the increased stress into useful longitudinal motion. Temperature rises and causes both the fatigue strength and the proportional limit to go down. Sound transmission characteristics may also change. In the case of higher proportional limit and higher modulus, there is a greater tendency then for the wire to break, to lose power at a bend, and to heat the attachment point. Conversely, a lower modulus has a compounding advantageous effect by avoiding unwanted vibration, due to high stress, and the resulting heat generation. Reducing losses and heat is particularly important if the sonic wire is placed in an artery where it cannot be easily cooled by "running water". A lower modulus provides yet another desirable metal property. The wire can be strained more easily and is less stiff or energy absorbing on being bent or threaded through the arterial system.

The property of lower modulus alone, however, was still not enough to produce a completely workable ultrasonic system where flexibility and bending was necessary. It was found also that a particular wire diameter was required depending upon the specific application. Diameters much larger or smaller than just under 1 mm were not useful in most blood vessel applications, for example. At diameters much above 1 mm, the wire, when bent appeared too stiff, became energy absorbing, and a great deal of sound energy wasted. When wire diameter becomes too small, a transverse degree of freedom appears allowing the wire to vibrate laterally like a plucked string. This motion tends to stress the wire particularly at its point of attachment to the horn.

In order to achieve high axial displacement amplitudes, the method of attachment of the wire to the horn must be smooth and symmetrical so as neither to absorb nor to reflect energy, and to minimize transverse waves. Two novel ways of wire attachment were found to be successful as will be explained.

All unwanted vibrations or harmonics are detrimental because they cause reflections and generate both heat and lateral motion in the wire. These harmonics and transverse (side-to-side) motions are not produced, or are not apparent, in standard laboratory ultrasonic horns and probes, but appear as the probe becomes thinner and more wire-like. In this present plaque application as well as in kidney stone breaking, the electronic generator and the horn feeding the wire both contribute to this non-linearity by producing or transmitting other than a perfectly clean fundamental wave. The standard step horn which gives the greatest amplitude to laboratory sonic probes was not the best choice for transmitting the generated energy into the smaller diameter wire. The conical horn was also not ideal. It was found that a horn with a non-linear taper, sometimes called an exponential horn, worked best for this purpose. The exponential horn either did not produce unwanted frequencies and harmonics, or attenuated them sufficiently such that less were transmitted to the attached wire. When using an exponential horn to transmit sound energy, the wire could be operated above its previously maxium rated amplitude before breaking.

As mentioned, the attachment point of the wire to the horn is critical because the energy transmitted to the wire and load passes thru this junction, a point which is physically non linear. The desired axial standing wave produces an antinode here which fortunately is a point of minimum stress. However, all transverse waves in the wire produce a node, or point of maximum stress at the attachment. Any transverse flexing must therefore be stopped or damped since at high power levels it will cause the wire to break. This was accomplished by attaching a rigid tube or sleeve to nodal points on either side of the wire/horn attachment, thus greatly reducing any stress on the wire here.

The foregoing and other objects, features and advantages will be apparent from the following description of the preferred embodiment of the invention as illustrated in the accompanying drawings.

DESCRIPTION OF THE PREFERRED EMBODIMENT

Figures 1, 2:
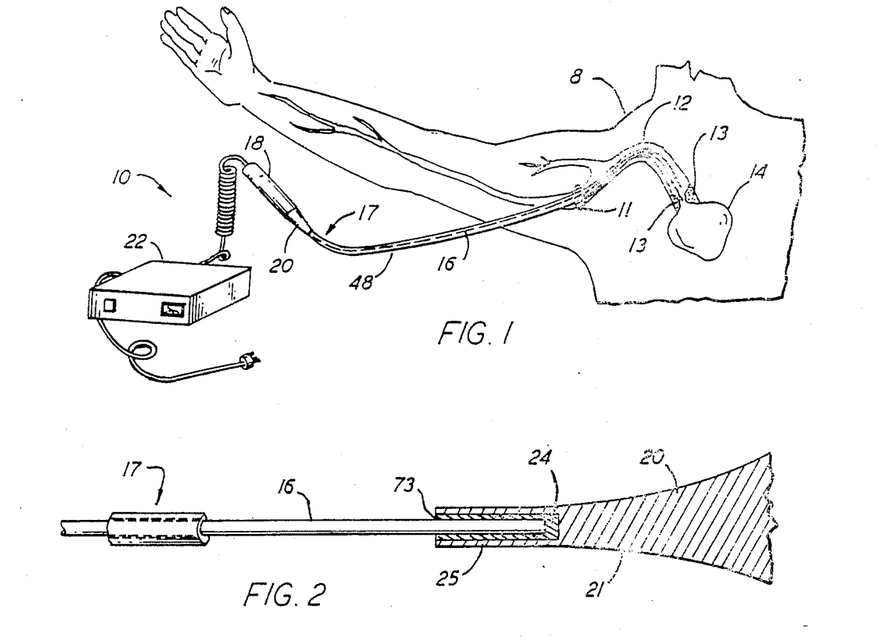
FIG. 1 is a perspective view of an ultrasonic device being used to remove plaque in a human being according to the invention.
FIG. 2 is an enlarged section view of the wire attachment portion of FIG. 1.

As illustrated in FIG. 1, a human being 8 is being treated by an ultrasonic device 10 of the present invention via an incision 11 in the armpit area and thence through a coronary artery 12 to a plaque deposit 13 therein. Artery 12 extends to the heart 14.

The ultrasonic device 10 has a wire 16 which acts as a waveguide that is positionably disposed within a catheter assembly 17. The wire 16 is maneuvered via the incision 11 through the artery 12 to be proximate the area of plaque 13 for removal thereof in a manner to be explained.

Referring now to FIGS. 1, 2, 4 and 5, device 10 also has a handpiece 18, that contains a piezoelectric or magnetostrictive converter or transducer 19 therein which produces ultrasonic energy and transmits it to the wire 16, and a generator 22 which energizes the transducer 19. Handpiece 18 has an exponential horn or tapered portion 20, which has a surface 21 that has an exponential concave profile. Handpiece 18 also has an elongate drilled hole 24 that receives an inner end of wire 16. A solder joint material 25 is present in the region between an inner surface of hole 24 and an outer surface of wire 16 adjacent thereto. The thickness of the solder material 25 shown in FIG. 2 is exaggerated for ease of illustration.

In the first novel process of attaching the wire 16 to the horn 20, the mating surfaces of hole 24 and wire 16 are first coated with a brazable material such as nickel or copper by a plating process such as electroplating or electroless plating. With both mating surfaces now coated, the wire 16 can be brazed or soldered by conventional means, resulting in a strong continuous bond to the horn 20. Thus, the wire 16 and tapered portion 20 are joined, so as to prevent any relative distortion or deflection therebetween, and so as to form a continuous, non-interrupted metal material for ease of transmission of vibration. The joint at solder material 25 is long enough to withstand the vibration energy applied thereat and does not cause any substantial reflection of the waves of vibration passing therethrough.

A second alternative novel method of attachment of the wire 16 to the horn 20 is by a friction fit or shrink fit. In the process of manufacture, a hole 24 slightly smaller than the diameter of the wire 16 is first drilled into the end 73 of the horn 20. The end 73 of the horn 20 is heated and the wire 16 is cooled. With the wire 16 held securely, for example in a collet (not shown), the horn 20 is slowly forced or tapped onto the wire 16. When both wire 16 and horn 20 return to the ambient temperature, the wire 16 expands and the metal around the hole 24 contracts to form a bond strong enough to withstand the high energy of vibration.

Wire 16 is composed of titanium metal. The characteristics of the wire 16 including the length and diameter depend upon the specific application. For use in the human body, for example, the overall length of the wire 16 is in the range of about 5 inches (12.7 centimeters) to 40 inches (101.6 centimeters) while the range of effective wire diameters is about 0.015 inches (0.381 millimeters) to 0.040 inches (1.016 millimeters). At diameters much below this range, the wire tends to break at high intensities since the sound wave is more easily diverted to what seemed to be transverse or whipping motion, rather than the longitudinal motion which produces cavitation. At diameters much above 1 mm, the wire, when bent appeared too stiff, became sound absorbing, and a great deal of sound energy wasted. In order to reach and enter the coronary arteries, as opposed to leg arteries, a diameter as small as possible or close to 0.020 inches (½ mm) is advisable.

The sound losses in a bent wire are:

$$Losses = K(D/R),$$

where D is the diameter of the wire, R is the radius of the bend and K a constant. The larger the diameter of the wire or smaller the bend radius, the more the sound wave differs in the time it takes to move from one point to another through the length of the wire. The path length along the inside bend radius is shorter than that along the outside and this distorts the wave front. Furthermore, the stress on the metal also varies between the inner and outer circumference; the inner being under compression and the outer under tension. This difference in stress alters the density and therefore the speed of sound in the wire. All the above changes produce nonlinearity of transmission and result in heating, harmonics, and lateral motion. Accordingly, the diameter has to be kept as small as possible in order to minimize these losses.

Thinner wire, below 1 mm in diameter, although producing fewer losses due to a lower D/R ratio, becomes highly susceptible to transverse waves that naturally appear, even without bending or high amplitudes and the wire will vibrate laterally. This motion tends to stress the wire particularly at its point of attachment to the horn.

The frequency is important in that the stresses and heat dissipation increase in the wire as the sound frequency is raised. This is due to the greater acceleration of the wire molecules. Below about 20 Khz however, high pitched noise may become objectionable. For a given power level, the lower the frequency, the higher the cavitation intensity.

Figure 3:
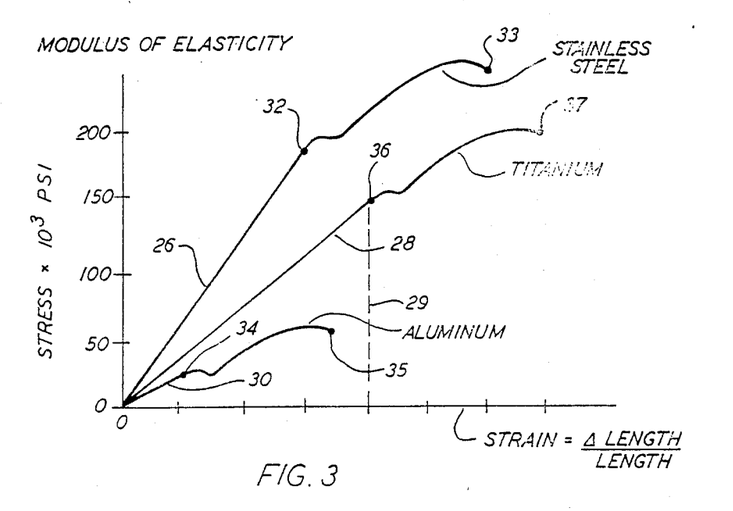
FIG. 3 is a graph of stress versus strain curves of stainless steel, titanium and aluminum.

In FIG. 3, a conventional graph of stress versus strain is shown. The graph has an upper curve 26 for stainless steel which has a proportional limit point 32 and a failure point 33. The graph also has a lower curve 30 for aluminum which has a proportional limit point 34 and a failure point 35. The graph also has a middle curve 28 for titanium which has a proportional limit point 36 and a failure point 37. By observation and comparison of the three curves 26, 28, 30, it is concluded that for a given relatively high stress level, the middle curve 28 for titanium material provides the largest relative strain. Thus, for a given length of wire 16 composed of a titanium material, a maximum displacement of wire 16 at its outer tip portion would occur, thereby providing a maxium amount of cavitation or fluid bubble action for removing plaque 13 from artery 12.

In FIG. 3, the modulus of elasticity, which is the ratio of the stress to the strain, is indicated by the respective slopes of curves 26, 28, 30. By comparing the slopes of curves 26, 28, 30, the curve 28 for titanium material is again found to be more suitable, than curve 26 of stainless steel material or curve 30 of aluminum material, for the application discussed herein since it yields a larger strain or tip movement for a smaller applied stress or ultrasonic intensity.

In FIG. 3, vertical line 29 passing through the proportional limit point 36 of curve 28 of titanium material shows the maximum strain possible in wire 16 of titanium material. For a selected length of wire in this embodiment, the change in length of wire 16, corresponding to the strain at line 29, is about 0.008 inches per inch.

Figure 4:
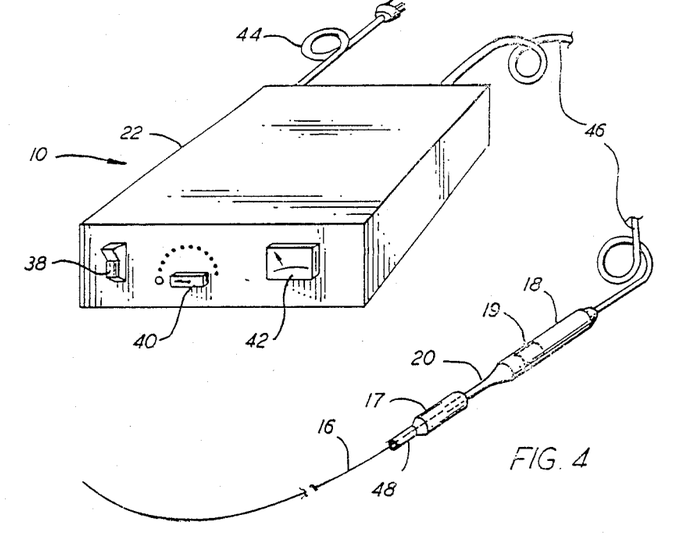
FIG. 4 is an enlarged perspective view of the ultrasonic device of FIG. 1.

In FIG. 4, an enlarged view of generator 22 is shown. Generator 22 has an on-off switch 38, a power setting control knob 40 and a power meter 42. Generator 22 also has a power line 44 for insertion in a conventional 110 volt outlet, and a connecting line 46 which extends from generator 22 to handpiece 18.

In operation, an operator, such as a surgeon, monitors the power meter 42 and applies low power at knob 40, during the surgical maneuvering of the outer tip end portion of wire 16 toward the plaque 13 to be removed in artery 12. Upon contact of the outer tip end portion of wire 16 with the plaque 13, which is indicated by an increase in the reading of meter 42, the operator applies high power at knob 40 for generating cavitation adjacent to the plaque or occlusion 13 for removing the plaque or occlusion. Alternatively, the operator can monitor the movement of the outer tip end portion of wire 16 toward the plaque to be removed in artery 12 by x-ray techniques, for example, by using a contrast medium in a manner to be explained.

Figure 5:
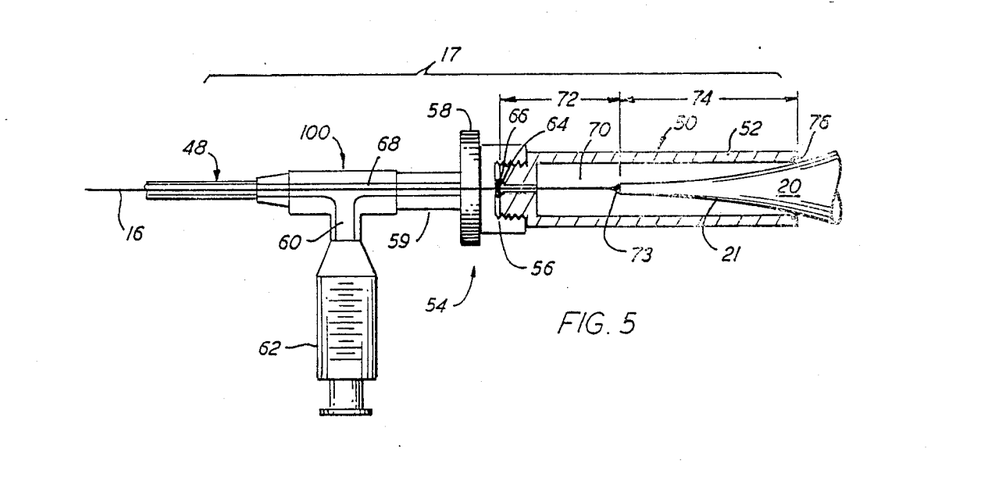
FIG. 5 is an enlarged section view of a portion of FIG. 4.

In FIG. 5, catheter assembly 17 includes a catheter tube 48, a container unit 50, a coupling unit 54, and a contrast fitting 100. The catheter tube 48 may be teflon or may have an inner surface of teflon or other inert material having a low coefficient of friction to slip easily over the wire 16. Container 50 includes a peripheral wall or sleeve 52 and a coupling unit 54. Coupling unit 54, which is somewhat similar to a coupling unit for a garden hose, has a fixed portion 56 which is fixedly connected to sleeve 52, and has a rotatable portion or knob portion 58 which is rotatable relative to fixed portion 56, in order to axially displace gliding sleeve 59 relative to fixed portion 56. Knob 58 is attached to portion 56 to permit rotation but no axial movement therebetween. Axial movement is imparted to sleeve 59 by rotation of knob 58. Catheter tube 48 is connected to contrast fitting 100 which is connected to portion 59 and moves relative to knob 58, for axial displacement of tube 48 relative to sleeve 52. In this way, by rotating knob 58, tube 48 is axially displaceable relative to wire 16, so that the outer tip portion of wire 16 can be slightly extended, when causing cavitation, beyond the outer tip portion of tube 48, which is normally flush for passing through artery 12.

Rotatable portion 58 has a seal means (not shown) in order to prevent leakage from coupling 54. Fixed portion 56 is fixedly connected to the adjacent portion of sleeve 52 and has a seal means in the form of O-ring 66 to prevent leakage from coupling 54.

Contrast fitting 100 has a hole 60, which receives a syringe 62 at its tip portion, for depositing an x-ray contrast fluid or medium from syringe 62 through hole 60 into a front chamber 68. Sleeve 52 has an inner annular projection 64, which supports the O-ring member 66. One purpose of the O-ring member 66 is to seal chamber 68, which contains the contrast fluid. O-ring member 66 separates front chamber 68 from rear chamber 70.

In FIG. 5, O-ring member 66 has an inner hole through which wire 16 passes. O-ring member 66 sealingly engages wire 16. The size of such hole in O-ring member 66 is exaggerated in FIG. 5 for ease of illustration. O-ring member 66 is located at a nodal point of wire 16 which is located at a selected dimension 72 away from the tip end face or attachment point 73 of tapered portion 20, as explained hereafter.

Container unit 50 also has a sealed connection 76 for connection of container unit 50 to tapered portion 20. Connection 76 may include an O-ring member on sleeve 52 which bears against a part of surface 21 of tapered portion 20. Connection 76 is at a nodal point of tapered portion 20 which is located at a selected dimension 74 away from the tip end face 73 of tapered portion 20, as explained hereafter.

O-ring member 66, which is at an axial nodal point of wire 16, is able to dampen the transverse force on wire 16 at that point when wire 16 is vibrated by the horn 20. O-ring member 66 does not substantially dampen the longitudinal vibration waves in wire 16. Thus, severe bending and relatively high stresses, at the region of wire 16 adjacent the attachment point to the end face 73 of the tapered portion 20, is avoided.

The nodal point in wire 16 at O-ring member 66 applies to both the transverse wave and longitudinal wave of vibration in wire 16. The nodal point has substantially no movement. An antinode point between two nodal points has a maximum movement. The point on wire 16 at the end face of tapered portion 20, or the wire attachment point, acts as an antinode point for the longitudinal wave of vibration, and acts as a nodal point for the unwanted transverse wave of vibration.

The operation of device 10 is explained hereafter. First, the percutaneous entry to the artery 12 is made in a conventional manner via incision 11. Then, tube 48 and wire 16 are passed through artery 12 of body 8 to the vicinity of the plaque 13. The operator, such as the surgeon, adjusts the generator 22 for low power on control knob 40, and watches the reading on meter 42, while passing the tube 48 and wire 16 toward the heart 14. When the plaque to be removed is contacted slightly, the reading on meter 42 changes. The surgeon then provides high power on control knob 40, thereby causing cavitation of fluid adjacent to the plaque. The surgeon may move the tip of wire 16 slightly toward the plaque 13 as the tissue is liquefied or dispersed.

Unless there is a total occlusion, the blood flow past the plaque 13 carries the minute particles of displaced plaque away. In the case of a total occlusion, the particles can be aspirated through the catheter assembly 17. Based upon in vitro experiments, it is expected that the sonicated particles removed from the plaque 13 will be below 15 microns and be absorbed or eliminated without great difficulty by the body.

A contrast medium is deposited in the fluid in front chamber 68 from syringe 62. The contrast medium passes through the catheter 48 to the tip of wire 16 at the site of the plaque 13. Conventional x-ray equipment, or the like, can form a picture of the tip of wire 16, the tip of tube 48, and the adjacent diseased portion of artery 12. The surgeon can make judgments on how to move the tip of wire 16, and where to position the tip of tube 48, and the like, during the removal of the plaque 13.

In the case of removal of a blood clot or other large occlusion, when there is little or no blood flow, the same procedure is followed with some exceptions. It may be desirable to remove the particles of the occlusion continuously. The syringe 62 can be removed from hole 60 and a conventional pump attached thereto, in order to aspirate the dispersed particles of the occlusion, from the site thereof through tube 48, to front chamber 68, and out through the pump. Tube 48 has a passage therethrough, of circular cross section, formed between the outer surface of wire 16 and the inner surface of tube 48.

Figure 6:
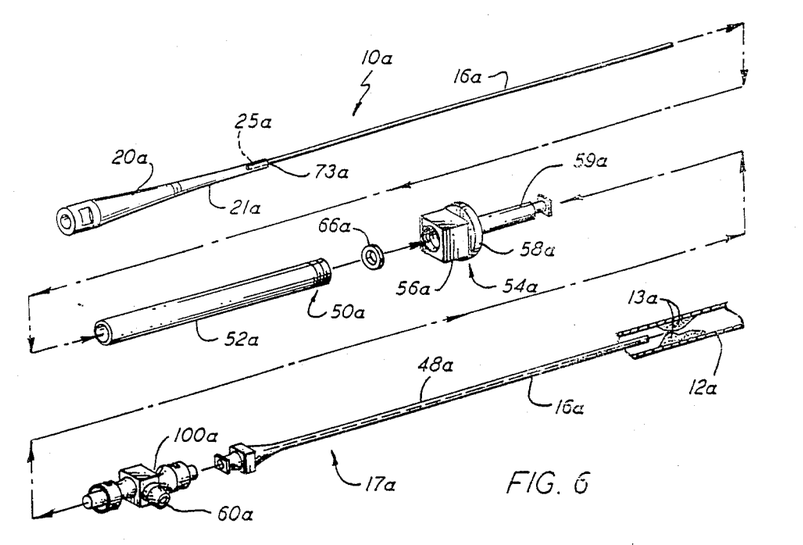
FIG. 6 is a disassembled perspective view generally of FIG. 5.

For purposes of further explanation, FIG. 6 provides a disassembled perspective view generally of that portion of ultrasonic device 10 shown in FIG. 5. Parts of device 10a, which correspond to similar parts of device 10, have the same numerals, but with a subscript "a" added thereto.

Device 10a includes a wire 16a, and a catheter assembly 17a. Device 10a has an exponential horn or tapered portion 20a, which has a surface 21a. Wire 16a is fixedly connected to tapered portion 20a by a solder joint 25a.

Wire 16a is composed of a titanium material. Wire 16a is a waveguide for longitudinal vibration waves from horn portion 20a. The longitudinal vibration waves cause an axial movement of the tip portion of wire 16a, thereby causing cavitation, which removes plaque 13a from artery 12a.

Catheter assembly 17a includes a catheter tube 48a, and a container or dampening unit 50a. Unit 50a has a sleeve or peripheral wall 52a and a coupling unit 54a. Unit 54a is used to axially displace wire 16a relative to catheter tube 48a, in order to extend an end portion of wire 16a, for working on plaque 13a in artery 12a. Coupling unit 54a has a fixed portion 56a, which is fixedly connected to sleeve 52a, and has a rotatable portion 58a, which is angularly movable relative to fixed portion 56a, for axially displacing catheter tube 48a.

Device 10a also has a fitting 100a, which is fixedly connected at one end thereof to a tubular member 59a that connects to rotatable portion 58a, and which is fixedly connected at the other end thereof to catheter tube 48a. Fitting 100a has a hole 60a, for receiving a syringe (not shown). A contrast medium may be added by the syringe to fluid in an elongate passageway of annular cross-section, which is formed between an outer surface of wire 16a and an inner surface of catheter tube 48a, in order to have a contrast medium in the fluid located next to plaque 13a.

Device 10a also has an O-ring 66a, which is positioned at a selected distance from the end face 73a of horn portion 20a. O-ring 66a is located at a nodal point of the longitudinal vibration wave which defines a nodal point of the transverse vibration wave, in order to minimize wire stresses at the end face 73a of horn portion 20a, and in order to prevent transverse movement or whipping of wire 16a at the location of the O-ring 66a.

Sleeve or dampening unit 50a has a connection to tapered horn portion 20a for assembly thereof.

Catheter tube 48a is composed of a suitable plastic material, such as teflon. Fitting 100a is composed of a stainless steel material. Sleeve 52a is composed of a suitable plastic material. Wire 16a is composed of a titanium material. Exponential horn 20a is composed of a titanium material. Coupling 54a is composed of a stainless steel or other suitable material.

Figure 7A:
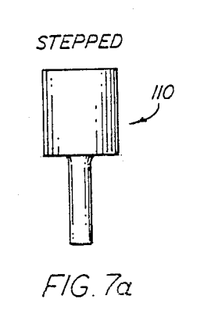
FIGS. 7a, b and c are perspective views showing various types of sonic horns which transmit and amplify the ultrasonic wave.
Figure 7B:
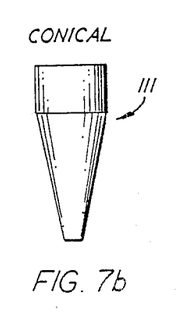
Figure 7C:
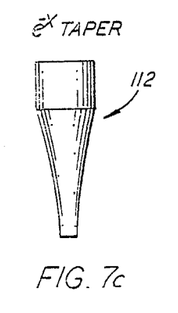

FIGS. 7a, b and c show various configurations of horns. In FIG. 7a, a standard step horn 110 is shown which provides the greatest amplitude for laboratory sonic probes but is not the best choice for transmitting energy into wire of the diameter used in the present application. In FIG. 7b, a conical shaped horn 111 is shown which is also less than ideal. In FIG. 7c, the exponential horn 112 having a taper $e^{-x}$ was best for the present application since unwanted frequencies and harmonics were minimized and the titanium wire described previously could be operated above its previously maximum rated amplitude before breaking.

There are a number of advantages to device 10 as indicated hereafter:
1. Device 10 has a flexible solid wire 16 which has dimensions and parameters suitable for entering body 8 and then passing through the body 8 to the arterial occlusion.
2. Wire 16 maintains a standing wave, transfers vibration energy, and provides a cavitation or bubble action at the site of occlusion for disintegration of the obstruction.
3. Fitting unit 100 provides a means to pass a contrast medium through artery 12 to the tip of wire 16 through tube 48 for obtaining an x-ray or flouroscopic picture while moving wire 16 and tube 48.
4. Wire 16 is a flexible solid wire composed of titanium metal, whereby relative maximum displacement of the tip of wire 16 is obtained resulting in relative maximum cavitation. This is due to the unique characteristics of the modulus of elasticity and the stress level possible.
5. Titanium wire 16 has bend portions with pronounced curvatures, caused by entry bends and artery bends, but wire 16 avoids corresponding portions of high stress and heating for longer life.
6. Device 10 has transverse wave nodal points at O-ring member 66, and at end face 73 of tapered portion 20, whereby stress at the end face 73 is minimized for longer life.
7. Exponential surface 21 of exponential tapered portion 20 minimizes unwanted frequencies in the vibration waves passing to wire 16, thereby avoiding heating of wire 16 especially at end face 73 and avoiding a whipping of wire 16 thereby minimizing wire fatigue and wire breakage.

There are a number of other advantages to device 10. Device 10 is believed to be useful in treating other diseases, as well as plaque or blood clots, as follows:
1. removing calcium from heart valves,
2. dispersing clumps of streptococcus bacteria on heart valves,
3. arrhythmia control by sonication of arrhythmia foci in the heart muscle,
4. clearing bile ducts,
5. removing tonsils
6. breaking gall stones,
7. shattering kidney stones and ureter stones, and
8. treating prostatic hypertrophy or prostate cancer.

Further, for example, device 10 can be used to sonicate or to provide a temporary hole in the heart wall or septum between the heart auricles of a newborn infant, where there is insufficient oxygenated blood at birth. This operation allows temporary bypass of oxygenated blood in the right auricle to pass to the left auricle. This temporary ultrasonic operation is performed prior to a conventional operation for the transposition of the main arteries of the newborn infant and results in minimal damage to the heart compared with the current techniques. This operation is performed using device 10 with the help of ultrasound scanning to provide imaging at the same time.

Although, the invention has been described primarily with respect to the removal of plaque in arteries of human beings, it will be appreciated that unwanted contaminants can be removed from inaccessible areas in industrial, commercial and even household applications by the use of an ultrasonic cavitation device 10.

For example, device 10 could be utilized on a production line for removal of unwanted production contaminants from inaccessible areas of finished or semi-finished products.

As another example, device 10 can be used as an industrial instrument, for removing unwanted material, such as the removal of caked grease in a minute passageway of a small component inside of an aerospace product of an aircraft, thereby avoiding the need for disassembly of the component and product.

While the invention has been described in its preferred embodiment, it is to be understood that the words which have been used are words of description rather than limitation and that changes may be made within the purview of the appended claims without departing from the true scope and spirit of the invention in its broader aspects.

The embodiments of an invention in which an exclusive property or right is claimed are defined as follows:

1. An ultrasonic device for use in removing an unwanted material from an artery of a human body by cavitation comprising:

a wire having a first end portion and having a second end portion for causing cavitation adjacent to the unwanted material;

support means having a handpiece having a tapered horn end portion with an integral metal joint fixedly connected to the first end portion of the wire;

drive means including a transducer supported by the handpiece for providing ultrasonic vibration through the tapered horn end portion to the wire and for connection to a generator; and a catheter assembly surrounding said wire and moveable relative to the wire to permit the second end portion of the wire to be positioned adjacent to the unwanted material; wherein said catheter assembly has a catheter tube and a container unit, said container unit including a peripheral wall and a front end wall portion and a rear end wall portion enclosing a cavity, said catheter tube having a first end portion connected to the container unit and having a second end portion disposed around the second end portion of the wire; and wherein said peripheral wall of said container unit has an annular interior partition projecting into said cavity, said partition having an O-ring member through which the wire passes, said O-ring member and partition forming a front sealed chamber and a separate rear chamber in said cavity; and wherein said O-ring member and partition are located at a selective distance from the tapered horn end portion, said location of the O-ring member being at a nodal point of a longitudinal wave of vibration of the wire, thereby minimizing transverse movement of the wire at the O-ring member and avoiding relatively high stress due to a transverse wave at the integral metal joint.

2. The device of claim 1, wherein
said wire has an overall length in the range of about 5 inches to 40 inches, and said wire has a uniform diameter in the range of about 0.015 inches to 0.040 inches, and said wire has a length to diameter ratio of a value about up to 2700.

3. The device of claim 1, wherein said wire is composed of a titanium alloy having a low modulus of elasticity.

4. The device of claim 1, wherein said tapered horn end portion has an exponential shaped outer surface.

5. The device of claim 1, wherein
said front end wall of said container unit forms a coupling unit,
said coupling unit having a fixed portion fixedly connected to said peripheral wall, said coupling having a rotatable portion movable along a longitudinal axis relative to the fixed portion when rotated, said rotatable portion being connected to the first end portion of said catheter tube, whereby the second end portion of said catheter tube can be moved relative to the second end portion of the wire, for extending the wire beyond the catheter tube during cavitation action.

6. The device of claim 5, wherein
said rear end wall of said container unit has a fixed connection to the tapered portion of the support means.

7. The device of claim 1, wherein
said container unit has a passage means extending from the exterior thereof to the front chamber, for passing an x-ray contrast medium into the fluid in the front chamber, and for passing of the contrast medium from the chamber through the catheter tube to the vicinity of the second end portion of the wire.

8. The device of claim 1, wherein
said container unit has a passage means extending from the exterior thereof to the front chamber for aspirating material through said catheter tube.

9. The device of claim 1, wherein
said integral metal joint is formed by the mating surfaces being initially coated with a brazable material by a plating process and then brazed or soldered together.

10. The device of claim 1, wherein
said integral metal joint is formed by a shrink fit between said wire and said tapered end portion.

11. An ultrasonic device for use in removing an unwanted material in a normally inaccessible area by cavitation comprising a relatively long, flexible wire having a first end portion and having a second end portion for causing cavitation adjacent to the unwanted material;

support means having a handpiece with a tapered horn end portion having an integral metal joint fixedly connected to the first end portion of the wire;

drive means including transducer means supported by the handpiece for providing ultrasonic vibration through the tapered horn end portion of the wire and for connection to a generator;

catheter assembly means surrounding said wire and having portions moveable relative to the wire to permit the second end portion of the wire to be positioned adjacent to the unwanted material; and transverse motion damping means disposed within the catheter assembly means and surrounding the wire for minimizing transverse motion of the wire and avoiding relatively high stress at the integral metal joint due to a transverse wave.

12. The device of claim 11, wherein said wire is composed of a titanium alloy having a low modulus of elasticity.

13. The device of claim 12, wherein said wire has an overall length in the range of about 5 to 40 inches and a uniform diameter in the range of about 0.015 to 0.040 inches.

14. The device of claim 11, wherein said tapered horn end portion has an exponential shaped outer surface.

* * * * *